(12) United States Patent
Ciriello et al.

(10) Patent No.: US 11,864,727 B2
(45) Date of Patent: Jan. 9, 2024

(54) AUTOMATED DENTAL TREATMENT SYSTEM

(71) Applicant: Cyberdontics (USA), Inc., San Francisco, CA (US)

(72) Inventors: Christopher John Ciriello, Castlegar (CA); Robert Joseph Ciriello, Ontario (CA); James Alexander Farwell, Ontario (CA)

(73) Assignee: Cyberdontics (USA), Inc., Boston, MA (US)

( * ) Notice: Subject to any disclaimer, the term of this patent is extended or adjusted under 35 U.S.C. 154(b) by 0 days.

(21) Appl. No.: 16/774,679

(22) Filed: Jan. 28, 2020

(65) Prior Publication Data

US 2020/0163729 A1    May 28, 2020

Related U.S. Application Data (63) Continuation of application No. 16/073,057, filed as application No. PCT/IB2017/000109 on Jan. 26, 2017, now abandoned.

(Continued)

(51) Int. Cl.
*A61B 34/30* (2016.01)
*A61C 9/00* (2006.01)
(Continued)

(52) U.S. Cl.
CPC .............. *A61B 34/30* (2016.02); *A61B 34/00* (2016.02); *A61B 34/10* (2016.02); *A61B 90/361* (2016.02);
(Continued)

(58) Field of Classification Search
CPC ......... A61B 34/30; A61B 34/00; A61B 34/10; A61B 34/25; A61B 90/361;
(Continued)

(56) References Cited

U.S. PATENT DOCUMENTS

| 3,772,790 A | 11/1973 | Swan-Gett et al. |
| 4,941,826 A | 7/1990 | Loran et al. |

(Continued)

FOREIGN PATENT DOCUMENTS

| CA | 2658807 A1 | 1/2008 |
| CN | 101883536 A | 11/2010 |

(Continued)

OTHER PUBLICATIONS

Fried et al.: Frailty in older adults: evidence for a phenotype. J Gerontol A Biol Sci Med Sci.; 56(3):M146-56 (2001).

(Continued)

*Primary Examiner* — Cris L. Rodriguez
*Assistant Examiner* — Drew S Folgmann
(74) *Attorney, Agent, or Firm* — Wilson Sonsini Goodrich & Rosati (57) ABSTRACT

An apparatus for performing dental surgery includes a central processing unit that controls automated operation of the apparatus and a display that renders an image of a target tooth requiring surgical intervention. The image of a target tooth being created from an image file received from the central processing unit. An input device receives surgical instructions from a user for providing the surgical intervention. The instructions are provided to the central processing unit for process. The surgical instructions include visual indications on the image of a target tooth that is to be treated. A robotic arm that includes an end effector is in communication with the central processing unit. The central processing unit controls the robotic arm to remove a region of the target tooth. The system also simultaneously mills the final tooth restoration in a separate milling chamber.

19 Claims, 10 Drawing Sheets

Related U.S. Application Data (60) Provisional application No. 62/287,212, filed on Jan. 26, 2016.

(51) Int. Cl.
| | | |
|---|---|---|
| *A61B 34/10* | (2016.01) | |
| *A61C 1/08* | (2006.01) | |
| *A61B 90/00* | (2016.01) | |
| *A61B 34/00* | (2016.01) | |
| *G16H 50/50* | (2018.01) | |
| *A61B 34/20* | (2016.01) | |
| *A61C 19/00* | (2006.01) | |

(52) U.S. Cl.
CPC .............. *A61C 1/082* (2013.01); *A61C 19/00* (2013.01); *G16H 50/50* (2018.01); *A61B 34/25* (2016.02); *A61B 2034/102* (2016.02); *A61B 2034/2048* (2016.02); *A61B 2034/2059* (2016.02); *A61B 2090/064* (2016.02); *A61B 2090/364* (2016.02); *A61B 2090/367* (2016.02); *A61B 2090/373* (2016.02)

(58) Field of Classification Search
CPC ...... A61B 2034/102; A61B 2034/2048; A61B 2034/2059; A61B 2090/064; A61B 2090/364; A61B 2090/367; A61B 2090/373; G16H 50/50; A61C 1/082; A61C 19/00; A61C 13/0004; A61C 5/77
See application file for complete search history.

(56) References Cited

U.S. PATENT DOCUMENTS

| | | | |
|---|---|---|---|
| 5,122,060 | A | 6/1992 | Vassiliadis et al. |
| 5,343,391 | A | 8/1994 | Mushabac |
| 5,516,286 | A | 5/1996 | Kushner |
| 5,888,065 | A | 3/1999 | Sussman |
| 6,049,743 | A * | 4/2000 | Baba .................. G16H 50/50 700/163 |
| 6,518,033 | B1 | 2/2003 | Gromeier et al. |
| 6,802,713 | B1 | 10/2004 | Chishti et al. |
| 8,251,984 | B2 | 8/2012 | Monty |
| 8,416,984 | B2 * | 4/2013 | Liang .................. G16H 10/60 382/100 |
| 8,716,973 | B1 | 5/2014 | Lammertse |
| 9,408,673 | B2 | 8/2016 | Monty |
| 9,622,833 | B2 | 4/2017 | Monty |
| 9,675,419 | B2 | 6/2017 | Akeel et al. |
| 9,788,915 | B2 | 10/2017 | Monty et al. |
| 10,016,242 | B2 | 7/2018 | Salcedo et al. |
| 10,568,499 | B2 | 2/2020 | Tesar |
| 10,792,133 | B2 | 10/2020 | Moon |
| 2005/0177266 | A1 * | 8/2005 | Kopelman ......... A61C 13/0004 700/117 |
| 2006/0127848 | A1 | 6/2006 | Sogo et al. |
| 2006/0153254 | A1 | 7/2006 | Franjic et al. |
| 2006/0166161 | A1 | 7/2006 | Rose et al. |
| 2006/0177796 | A9 | 8/2006 | Heasley |
| 2007/0265495 | A1 | 11/2007 | Vayser |
| 2008/0009697 | A1 | 1/2008 | Haider et al. |
| 2008/0096156 | A1 | 4/2008 | Rose et al. |
| 2008/0153067 | A1 | 6/2008 | Berckmans et al. |
| 2008/0276192 | A1 | 11/2008 | Jones et al. |
| 2009/0142724 | A1 | 6/2009 | Rosenblood et al. |
| 2009/0186318 | A1 | 7/2009 | Assa et al. |
| 2009/0187175 | A1 | 7/2009 | Assa et al. |
| 2009/0248184 | A1 | 10/2009 | Steingart et al. |
| 2009/0253095 | A1 | 10/2009 | Salcedo et al. |
| 2010/0105011 | A1 | 4/2010 | Karkar et al. |
| 2011/0143306 | A1 | 6/2011 | Hirsch et al. |
| 2012/0059378 | A1 * | 3/2012 | Farrell .................. A61B 90/25 606/80 |
| 2012/0231421 | A1 | 9/2012 | Boerjes et al. |
| 2013/0059264 | A1 | 3/2013 | Monty |
| 2013/0188012 | A1 | 7/2013 | Bellis et al. |
| 2013/0211242 | A1 * | 8/2013 | Bertrand .................. A61B 5/72 600/424 |
| 2013/0322719 | A1 | 12/2013 | Dekel et al. |
| 2014/0107471 | A1 | 4/2014 | Haider et al. |
| 2014/0272767 | A1 | 9/2014 | Monty |
| 2014/0272773 | A1 | 9/2014 | Merritt et al. |
| 2014/0272775 | A1 | 9/2014 | Monty |
| 2015/0057576 | A1 | 2/2015 | Chen |
| 2015/0057675 | A1 | 2/2015 | Akeel et al. |
| 2015/0320320 | A1 | 11/2015 | Kopelman et al. |
| 2016/0135816 | A1 | 5/2016 | Lavallee et al. |
| 2016/0143703 | A1 | 5/2016 | Monty et al. |
| 2016/0149369 | A1 | 5/2016 | Monty et al. |
| 2016/0338803 | A1 | 11/2016 | Pesach |
| 2016/0354169 | A1 | 12/2016 | Suttin et al. |
| 2016/0367336 | A1 | 12/2016 | Lv et al. |
| 2017/0020636 | A1 | 1/2017 | Akeel et al. |
| 2017/0079746 | A1 | 3/2017 | Sanders |
| 2017/0319277 | A1 | 11/2017 | Cantor-Balan et al. |
| 2018/0078332 | A1 | 3/2018 | Mozes et al. |
| 2018/0325622 | A1 | 11/2018 | Groves, Jr. et al. |
| 2019/0029524 | A1 | 1/2019 | Kopelman et al. |
| 2019/0076026 | A1 | 3/2019 | Elbaz et al. |
| 2019/0151042 | A1 | 5/2019 | Holman et al. |
| 2019/0298448 | A1 | 10/2019 | Kerbage et al. |
| 2019/0336243 | A1 | 11/2019 | Di Sessa et al. |
| 2019/0388194 | A1 | 12/2019 | Atiya et al. |
| 2020/0178811 | A1 | 6/2020 | Shindo |
| 2020/0315754 | A1 | 10/2020 | Ciriello et al. |
| 2020/0390518 | A1 | 12/2020 | Ciriello et al. |
| 2021/0169318 | A1 | 6/2021 | Sorimoto et al. |
| 2021/0186667 | A1 | 6/2021 | Abu-Tarif et al. |
| 2021/0205633 | A1 | 7/2021 | Kerbage et al. |
| 2021/0228317 | A1 | 7/2021 | Ciriello et al. |

FOREIGN PATENT DOCUMENTS

| | | |
|---|---|---|
| CN | 105832419 A | 8/2016 |
| CN | 107205795 A | 9/2017 |
| DE | 10145104 A1 | 1/2003 |
| DE | 102005043402 A1 | 3/2007 |
| DE | 202010003663 U1 | 7/2010 |
| EP | 0553712 A1 | 8/1993 |
| EP | 2078493 A2 | 7/2009 |
| EP | 2459115 A2 | 6/2012 |
| EP | 2722003 A1 | 4/2014 |
| EP | 3288486 A1 | 3/2018 |
| EP | 3391810 A1 | 10/2018 |
| EP | 3476357 A1 | 5/2019 |
| FR | 2804859 A1 | 8/2001 |
| JP | 2007244494 A | 9/2007 |
| KR | 20210122584 A | 10/2021 |
| RU | 2443396 C1 | 2/2012 |
| WO | WO-2004074324 A2 | 9/2004 |
| WO | WO-2007072866 A1 | 6/2007 |
| WO | WO-2007078512 A2 | 7/2007 |
| WO | WO-2011014802 A2 | 2/2011 |
| WO | WO-2011021192 A1 | 2/2011 |
| WO | WO-2012004018 A1 | 1/2012 |
| WO | WO-2012105972 A1 | 8/2012 |
| WO | WO-2013172919 A1 | 11/2013 |
| WO | WO-2014024157 A1 | 2/2014 |
| WO | WO-2014035010 A1 | 3/2014 |
| WO | WO-2015009856 A2 | 1/2015 |
| WO | WO-2015026546 A2 | 2/2015 |
| WO | WO-2015134633 A1 | 9/2015 |
| WO | WO-2015188286 A1 | 12/2015 |
| WO | WO-2016022347 A1 | 2/2016 |
| WO | WO-2016040657 A1 | 3/2016 |
| WO | WO-2016093984 A1 | 6/2016 |
| WO | WO-2016108276 A1 | 7/2016 |
| WO | WO-2016113745 A1 | 7/2016 |
| WO | WO-2016145093 A1 | 9/2016 |
| WO | WO-2016154589 A1 | 9/2016 |
| WO | WO-2016178212 A1 | 11/2016 |
| WO | WO-2017100828 A1 | 6/2017 |
| WO | WO-2017130060 A1 | 8/2017 |

(56) References Cited

FOREIGN PATENT DOCUMENTS

| WO | WO-2018012862 A1 | 1/2018 |
|----|------------------|--------|
| WO | WO-2018154485 A1 | 8/2018 |
| WO | WO-2018198095 A1 | 11/2018 |
| WO | WO-2019021718 A1 | 1/2019 |
| WO | WO-2019093426 A1 | 5/2019 |
| WO | WO-2019153413 A1 | 8/2019 |
| WO | WO-2019209637 A1 | 10/2019 |
| WO | WO-2019215511 A2 | 11/2019 |
| WO | WO-2019215512 A1 | 11/2019 |
| WO | WO-2021044218 A1 | 3/2021 |
| WO | WO-2021155045 A1 | 8/2021 |
| WO | WO-2021257708 A1 | 12/2021 |
| WO | WO-2022051516 A1 | 3/2022 |
| WO | WO-2022060800 A1 | 3/2022 |

OTHER PUBLICATIONS

Geomagic Sculpt website http://www.geomagic.com/en/products/sculpt/touch/ (automatically redirected to http://www.geomagic.com/en/products/sculpt/touch/), accessed Oct. 2, 2018.
Yuan et al.: An automatic tooth preparation technique: A preliminary study; Scientific Reports|6:25281 |DOI:10.1038/srep25281, pp. 1-9 (2016).
PCT/IB2017/000109 International Preliminary Report on Patentability dated Jul. 31, 2018.
PCT/IB2017/000109 International Search Report and Written Opinion dated Jun. 14, 2017.
PCT/IB2018/051115 International Search Report and Written Opinion dated Jun. 5, 2018. .
PCT/IB2019/000578 International Preliminary Report and Written Opinion dated Nov. 18, 2019.
U.S. Appl. No. 16/073,057 Office Action dated Jul. 31, 2019.
Visuri et al.: Shear Strength of Composite Bonded to Er:YAG Laser-prepared Dentin. J Dent Res; 75(1):599-605 (1996).
Fried et al.: Ablation of Dental Hard Tissues with a Microsecond Pulsed Carbon Dioxide Laser Operating at 9.3-μm with an Integrated Scanner. Proc SPIE Int Soc Opt Eng. 6843:16 pages (2008).
European Patent Application No. 18757107.0 European Search Report dated Feb. 4, 2021.
Kim et al.: Improved accuracy in periodontal pocket depth measurement using optical coherence tomography. J Periodontal Implant Sci. 47(1):13-19 (2017).
Le et al.: A non-invasive imaging and measurement using optical coherence tomography angiography for the assessment of gingiva: An in vivo study. J Biophotonics. 11(12) (2018).
PCT/IB2020/000729 International Search Report and Written Opinion dated Dec. 31, 2020.
Tsubokawa et al.: In vitro and clinical evaluation of optical coherence tomography for the detection of subgingival calculus and root cementum. J Oral Sci. 60(3):418-427 (2018).
U.S. Appl. No. 17/000,175 First Action Interview dated Mar. 22, 2021.
PCT/US2021/015555 International Search Report and Written Opinion dated Apr. 14, 2021.
PCT/US2021/037635 Invitation to Pay Additional Fees dated Aug. 24, 2021.
U.S. Appl. No. 17/000,175 Final Office Action Aug. 24, 2021.
U.S. Appl. No. 17/000,175 First Action Interview dated Jun. 4, 2021.
Kauer et al.: Clinical evaluation of effects of low-level lasers on pain during cavity preparation. International Journal of Research—Granthaalayah. 6(10):81-86 (2018).
PCT/IB2019/000578 International Preliminary Report on Patentability dated Nov. 10, 2020.
PCT/US2021/037635 International Search Report and Written Opinion dated Nov. 26, 2021.
PCT/US2021/048893 International Search Report and Written Opinion dated Dec. 7, 2021.
PCT/US2021/050413 International Search Report and Written Opinion dated Dec. 23, 2021.
U.S. Appl. No. 17/000,175 Office Action dated Jan. 11, 2022.
EP19800428.5 Extended European Search Report dated Feb. 22, 2022.
U.S. Appl. No. 17/054,445 Office Action dated Feb. 18, 2022.

* cited by examiner

AUTOMATED DENTAL TREATMENT SYSTEM

CROSS-REFERENCE TO RELATED APPLICATIONS

This application is a continuation of U.S. application Ser. No. 16/073,057, filed Jul. 26, 2018, which is the U.S. National Phase entry of International Application No. PCT/IB2017/000109, filed Jan. 26, 2017, which claims the benefit of U.S. Provisional Application No. 62/287,212 filed Jan. 26, 2016, each of which are incorporated by reference herein in their entireties.

TECHNICAL FIELD

In at least one aspect, the present invention is related to robotically controlled systems for treating dental disease.

BACKGROUND

Although advances have been made in recent years for the treatment of specific dental diseases, the actual delivery of dental treatment remains a manually intensive process. Accordingly, there is a need for methodology for automating dental treatment.

SUMMARY

The present invention solves one or more problems of the prior art by providing in at least one embodiment, an apparatus for performing dental surgery on a subject. The apparatus includes a central processing unit that controls automated operation of the apparatus and a display that renders an image of a target tooth requiring surgical intervention. The image of a target tooth being created from an image file received from the central processing unit. An input device receives surgical instructions from a user for providing the surgical intervention. The instructions are provided to the central processing unit for process. The surgical instructions include visual indications on the image of a target tooth that is to be treated. A robotic arm that includes an end effector is in communication with the central processing unit. The central processing unit controls the robotic arm to remove a region of the target tooth.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The term "subject" as used herein refers to a human patient in need of dental treatment.

The term "STL" is a file format for stereolithographic CAD software.

Figure 1:
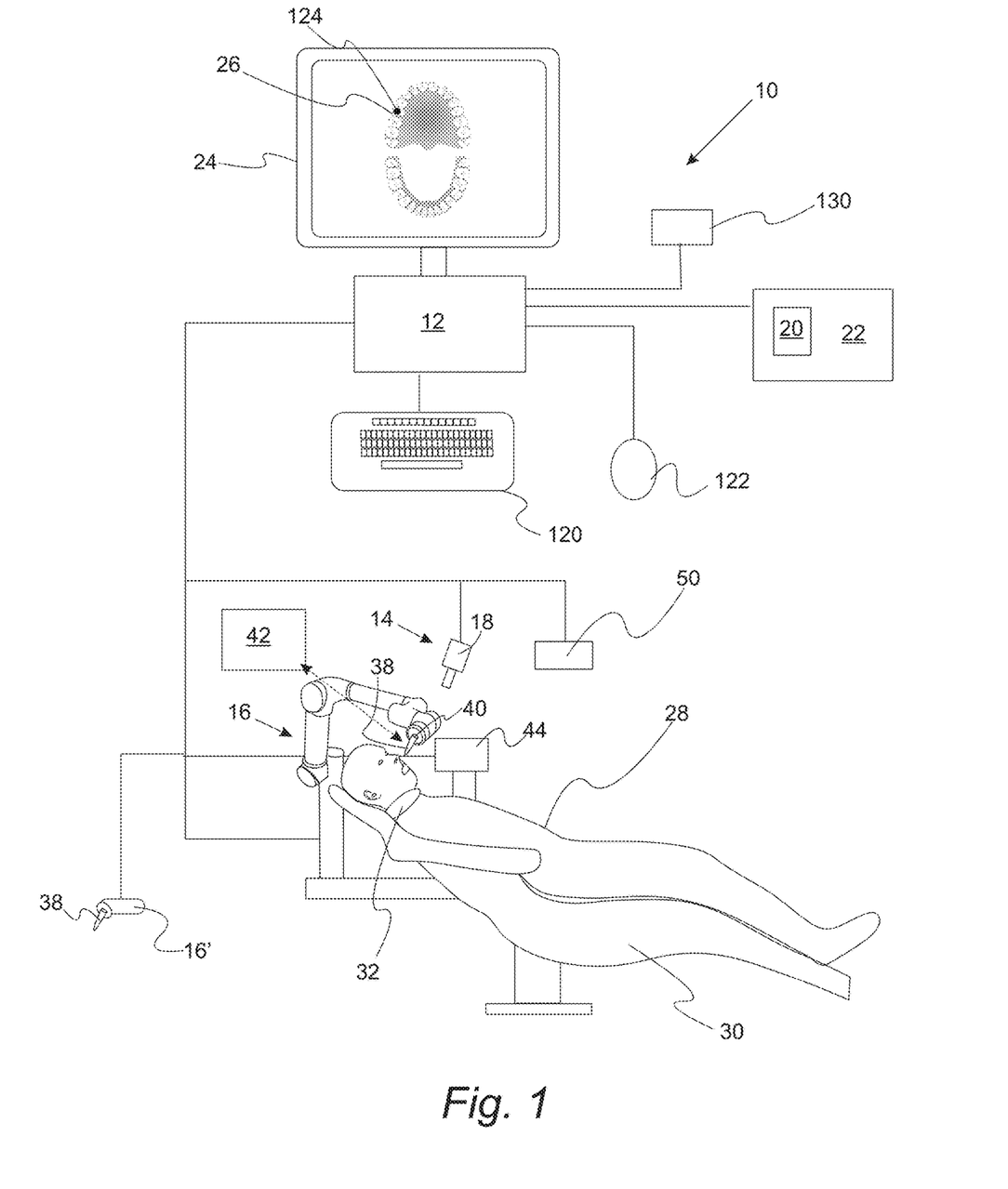
FIG. 1 is a schematic illustration of a dental treatment system.

With reference to FIG. 1, a schematic illustration of an automated dental treatment system is provided. Dental treatment system 10 includes central processing unit 12 in communication with tooth scanner 14 and robotic arm 16. An example of a useful robotic arm is a 6 DOF robotic arm such as the Universal Robotics Arm. In another refinement, robotic arm 16 is a hand held device 16' with robotic movement features to be held by the user. In a refinement, tooth scanner 14 includes user handle for a user to hold and move the scanner as needed. Central processing unit 12 controls automated operation of the dental treatment system 10. Typically, central processing unit 12 is contained in a computer work station. Control program(s) 20 which resides in computer memory 22 is executed by central processing unit 12 to receive image files from scanner 14 and to control the movement of robotic arm 16. During operation, tooth scanner 14 can transfer tooth image data to the central processing unit 12. The central processing unit 12 includes a display 24 on which the surgical process is guided through a series of onscreen prompts. Display 24 renders an image 26 of a target tooth in subject 28 from an image file requiring surgical intervention. FIG. 1 depicts subject 28 sitting in dental chair 30. Subject 28's head is immobilized by head restraint 32. Robot arm 16 includes an end effector 38 for performing dental surgery. End effector 38 is typically a numerically controlled dental drill. Coupler 40 is used to attach a conventional high speed electric dental hand piece to the robotic arm 16 with no slop. In a refinement, tool changer 42 allows automatic tool change of burs for robotic arm. In this regard, tool changer 42 will search out end-effectors, match appropriate end-effectors, and change the end-effectors. In another refinement, dental treatment system 10 includes passive positioning encoder arm 44 which tracks the patient position and relays it to central processing unit 12.

Figure 2:
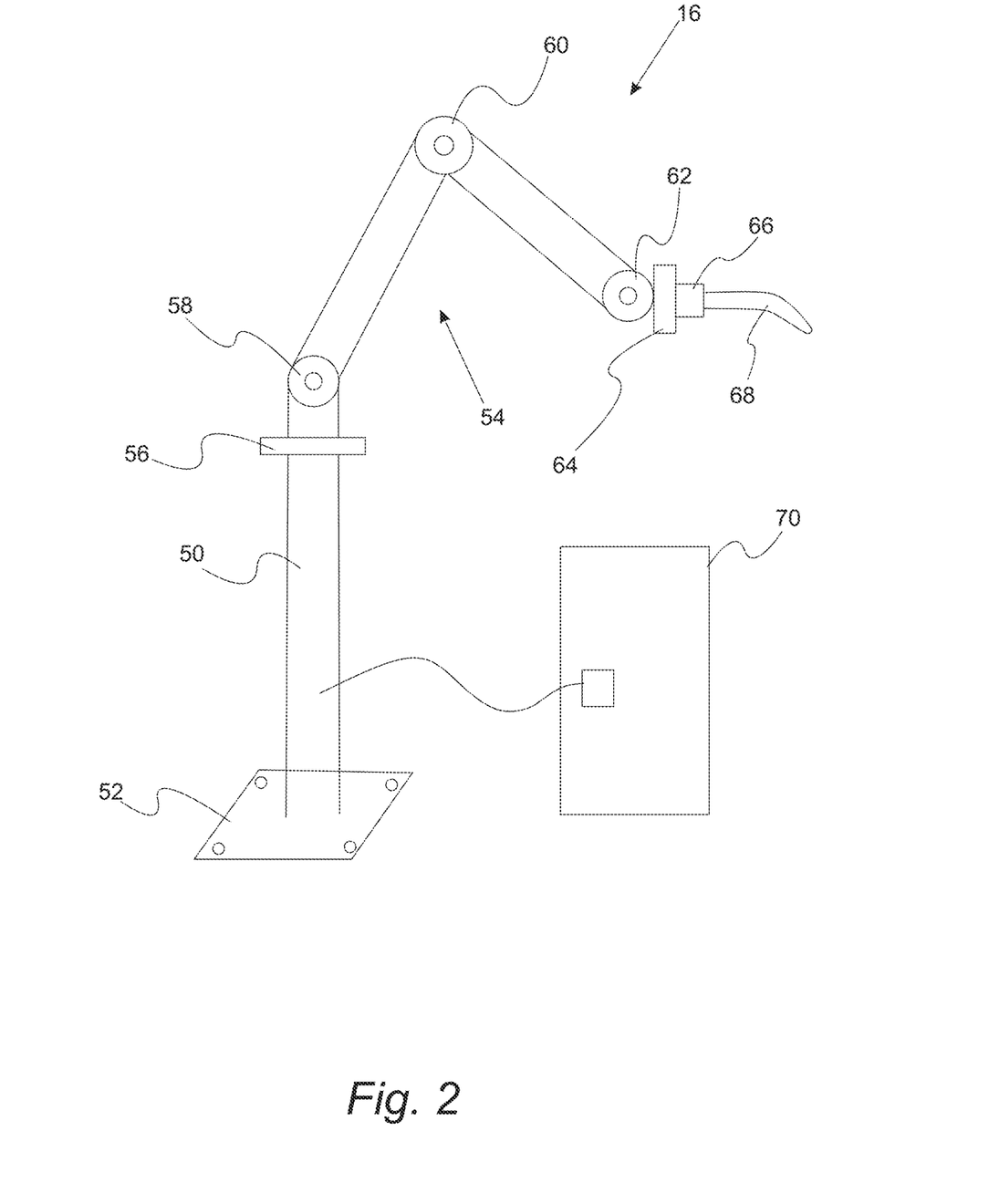
FIG. 2 is a schematic illustration of a robotic arm used in the dental treatment system of FIG. 1.

With reference to FIGS. 1 and 2, dental treatment system 10 includes robot arm 16. Robotic arm 16 consists of a multi jointed arm with allow precision movement of end effector 44. Robotic arm 16 includes support column 50 mounted on base plate 52. Robotic arm 16 includes movable arm section 54 which includes 5 axes of rotation—axis 56-64. Robotic arm 16 also includes quick change tool coupling 66 which attaches to drill hand piece 68. Robot control 70 is in electrical communication with robotic arm 16 and with central processing unit 12.

Figure 3:
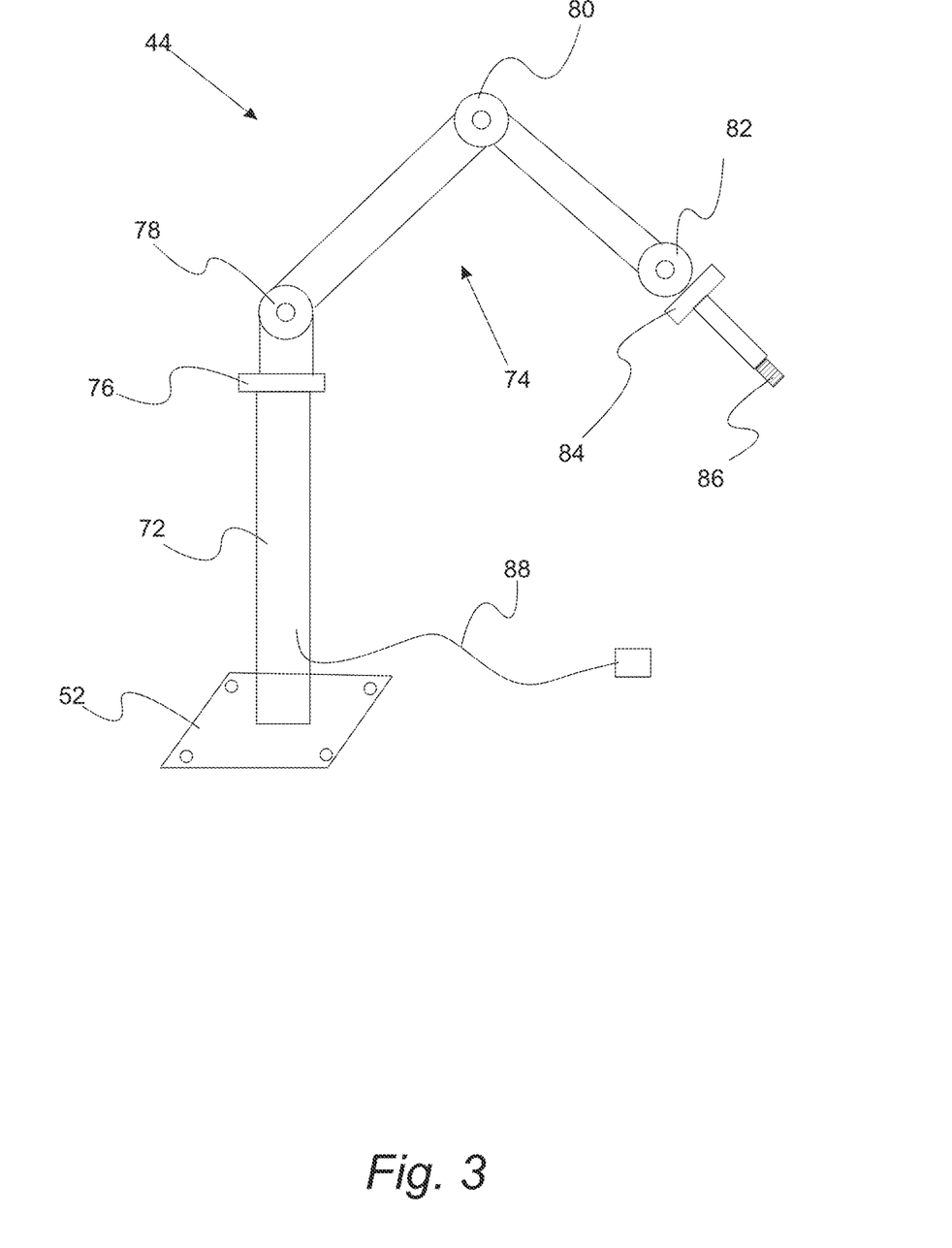
FIG. 3 is a schematic illustration of a passive positioning encoder arm used in the dental treatment system of FIG. 1.

With reference to FIGS. 1 and 3, passive positioning encoder arm 44 is schematically illustrated. Passive positioning encoder arm 44 tracks the subject's head motion and tooth motion. Encoder arm 44 consists of a multi jointed arm with encoders to generate a 3D position of its end effector. It is rooted a specific point relative to the robotic arm, and clamped to a tooth posterior to the tooth being worked on surgically. An example for passive positioning encoder arm 44 it depicted in FIG. 2. In this example, passive positioning encoder arm 44 includes support column 72 mounted on base plate 42. In a refinement, base plate 42 and also be used to mount robotic arm 16. Passive positioning encoder arm 44 includes movable arm section 74 which includes 5 axes of rotation—axis 76-84. Passive positioning encoder arm 44 also includes a quick connect 86 that attaches to a modified rubber dam clamp with is the end effector of the encoder arm. Passive positioning encoder arm 44 also includes sensor output cable 88 which is used to transfer positioning information to central processing unit 12. The encoder arm includes encoders that generate a 3D position of the end effector (i.e., the modified rubber dam clamp). Passive positioning encoder arm 44 is passive with respect to reciprocal forces generated on the modified rubber dam clamp as the subject moves and that movement is met with no resistance by the passive arm. If the subject moves and a force is applied to the rubber dam clamp, that force is then transferred to the positioning arm, and any resistance to its movement would generate a reciprocal force to the rubber dam clamp. If the clamp moves relative to the tooth, it throws off the positioning method for the robotic cutting arm, requiring a re-scan and calibration. Therefore, it is advantageous to minimize this force to as close as zero as possible by making its passivity and resistance to movement a design priority. In a refinement, encoder arm 44 senses fast movements by the subject that trigger a shutdown procedure. In another variation, encoder arm 44 is operable to being shut down by the subject (i.e., by a switch).

Figure 4:
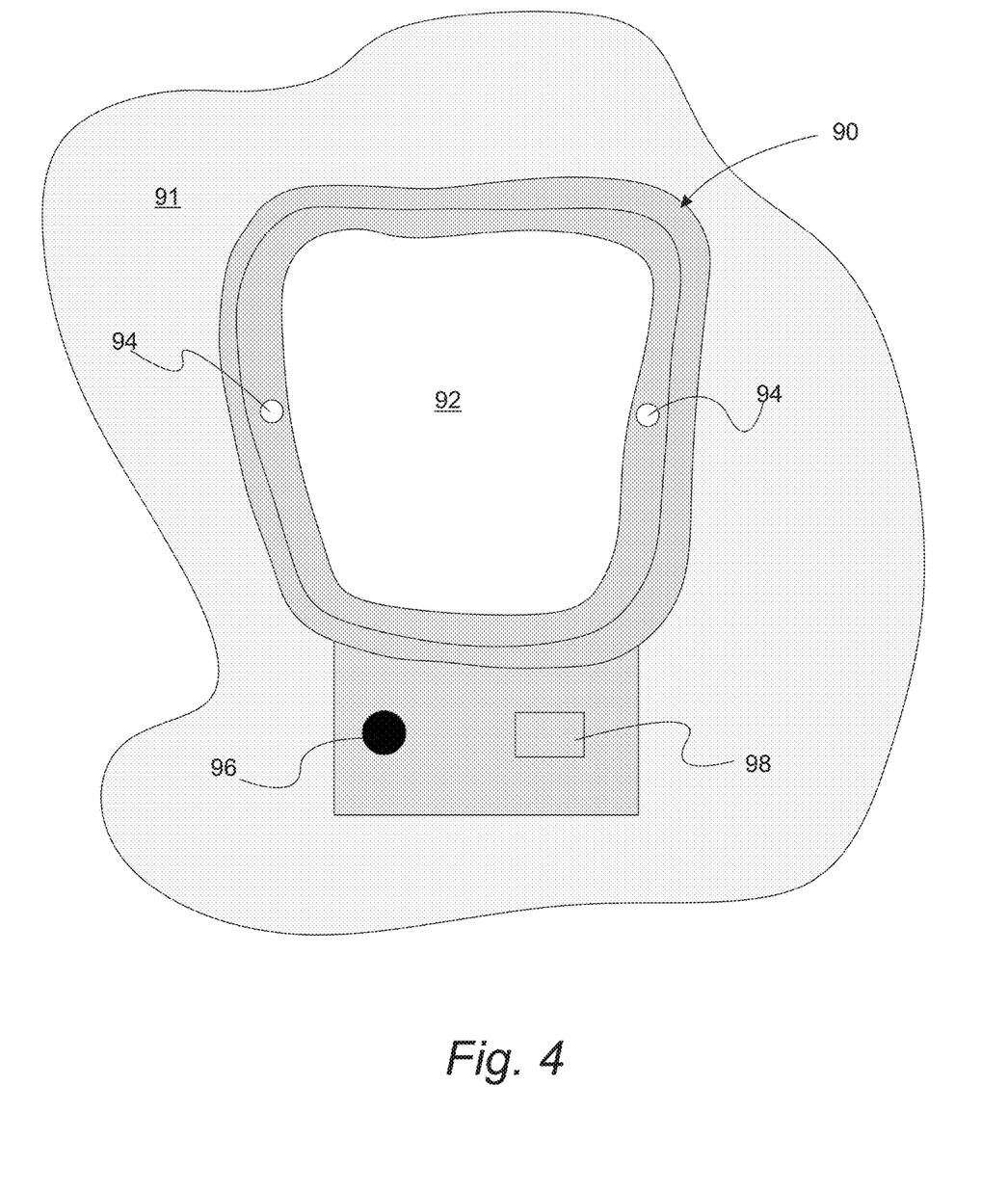
FIG. 4 is a schematic illustration of a modified rubber dam clamp used in the dental treatment system of FIG. 1.

With reference to FIG. 4, a schematic of a modified rubber dam to be used with dental treatment system 10 is provided. Rubber dam clamp 90 holds rubber dam 91 in place about a central opening 92 in which a tooth is to be positioned. Rubber dam clamp 90 includes forceps holes 94 to be used for placement and removal of the dam clamp. Locating datum point 96 is used to provide a positioning reference point that the robotic arm 16 routinely moves to ensure it is calibrated and that the modified rubber dam clamp positioning reference point has not shifted relative to the tooth during the procedure or patient movement. Attachment of rubber dam clamp 90 to passive encoder arm 44 is accomplished by a bar attached to quick connect 98. A number of design variations for rubber dam clamp 90 are possible. Examples of such designs include an even numbered quadrant molar clamp, an odd numbered quadrant molar clamp, and a premolar clamp.

Figure 5:
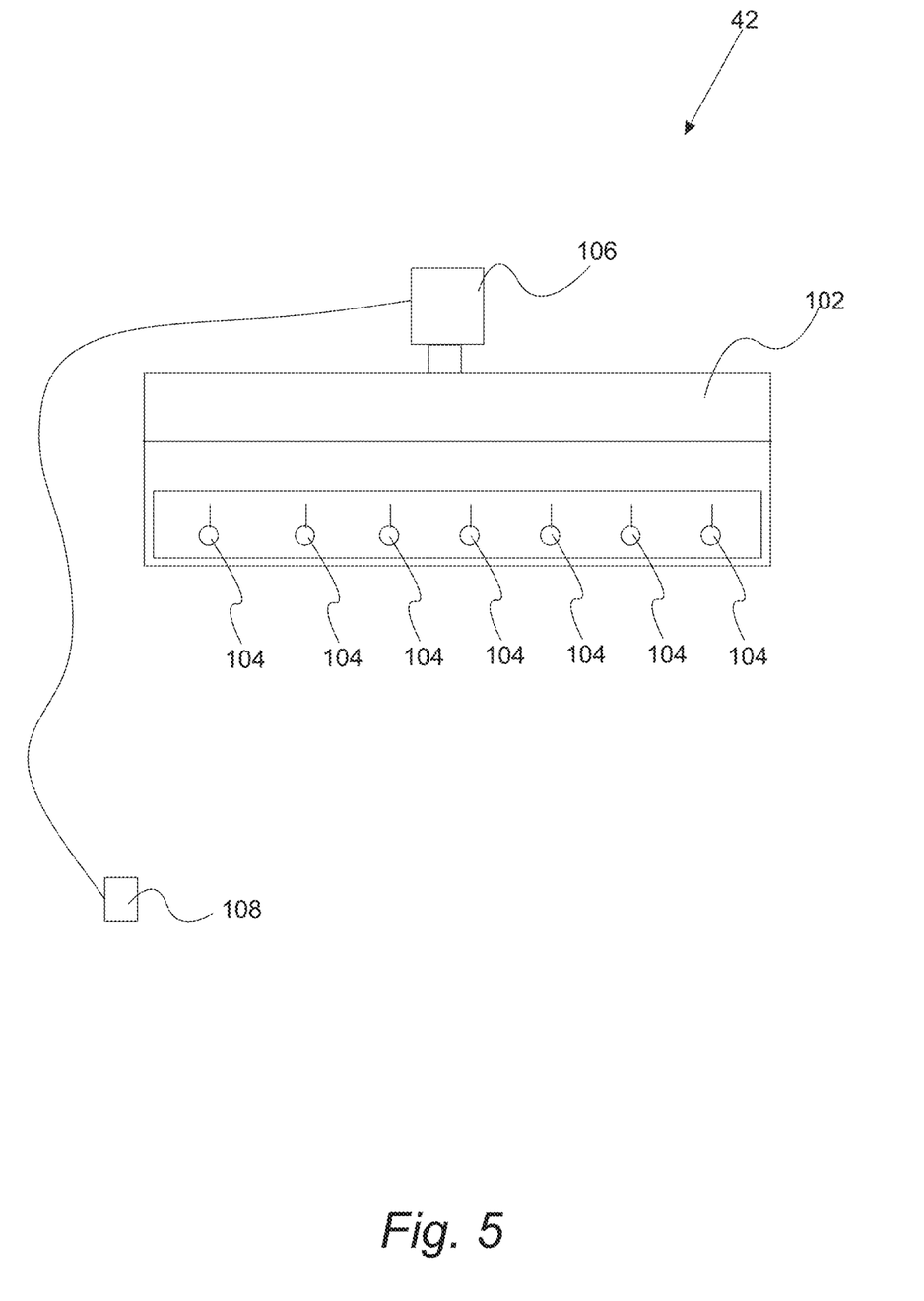
FIG. 5 is a schematic illustration of a tool changer used in the dental treatment system of FIG. 1.

With reference to FIG. 5, a schematic illustration of tool changer 42 is provided. Tool changer 42 includes contact bar 102 to release the drill spindles. Locations 104 are used to swap dental burs in and out of end effector 38. Tool changer 42 is pneumatically operated by air cylinder 106 which is supplied air from source 108.

Figure 6:
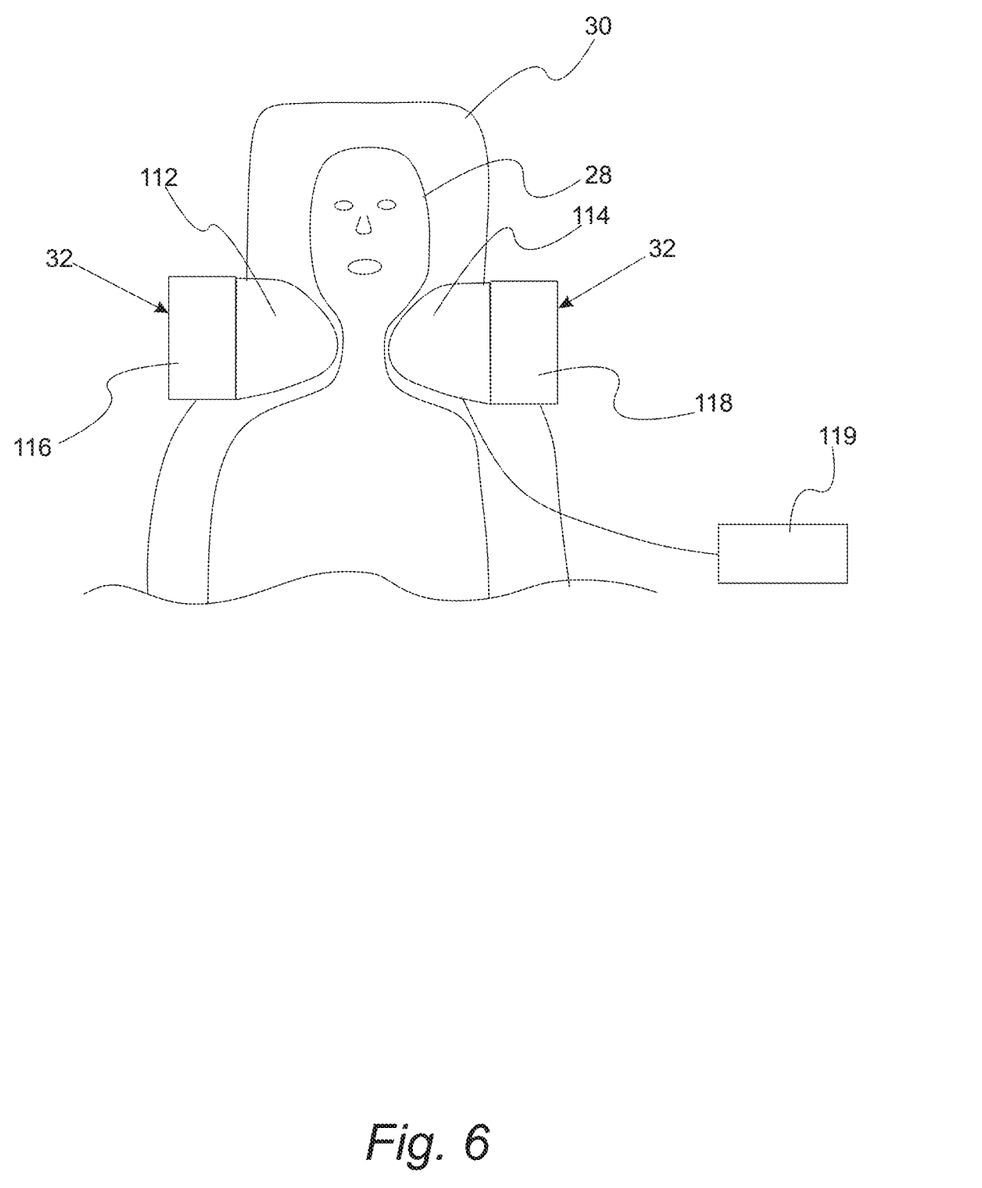
FIG. 6 is a schematic illustration of a head restraint used in the dental treatment system of FIG. 1.

With reference to FIG. 6, the positioning of head restraint 32 about subject 28's head is schematically illustrated. While subject 28 is seating in dental chair 30, head restraint 32 is positioned about the subject's neck contacting the base of the head so as to impede head movements. Head restraint 32 can allow a small amount of movement (e.g., 2-3 cm) for comfort while preventing large movements (e.g., >2-3 cm). Head restraint 32 incudes air bladders 112, 114 which are mounted on air bladder mounts 116, 118. Air bladders 112, 114 are inflated with air supplied from air source 119.

With reference to FIGS. 1-7, operation of dental treatment 10 is described as follows. Central processing unit 12 controls the robotic arm 16 to remove a region of the target tooth. Dental treatment system 10 includes input devices 120, 122 which can for example be a keyboard and mouse that receive surgical instructions from a user for providing the surgical intervention. The instructions are received by the central processing unit 12. Characteristically, the surgical instructions including visual indications 124 on the image of a target tooth that are to be treated. Control program 20 guides the user through the dental protocols through a series of onscreen prompts (i.e., the user interface). In this context, actions attributable to control program 20 is understood to mean the execution of the relevant steps by central processing unit 12. In a variation, dental treatment system 10 includes static memory 130 for storing patient profiles and records which can be accessed by the user. In a refinement, central processing unit 12 also displays a load screen that shows a series of patient records and gives the option to load an existing patient, or create a new patient record.

Figure 7:
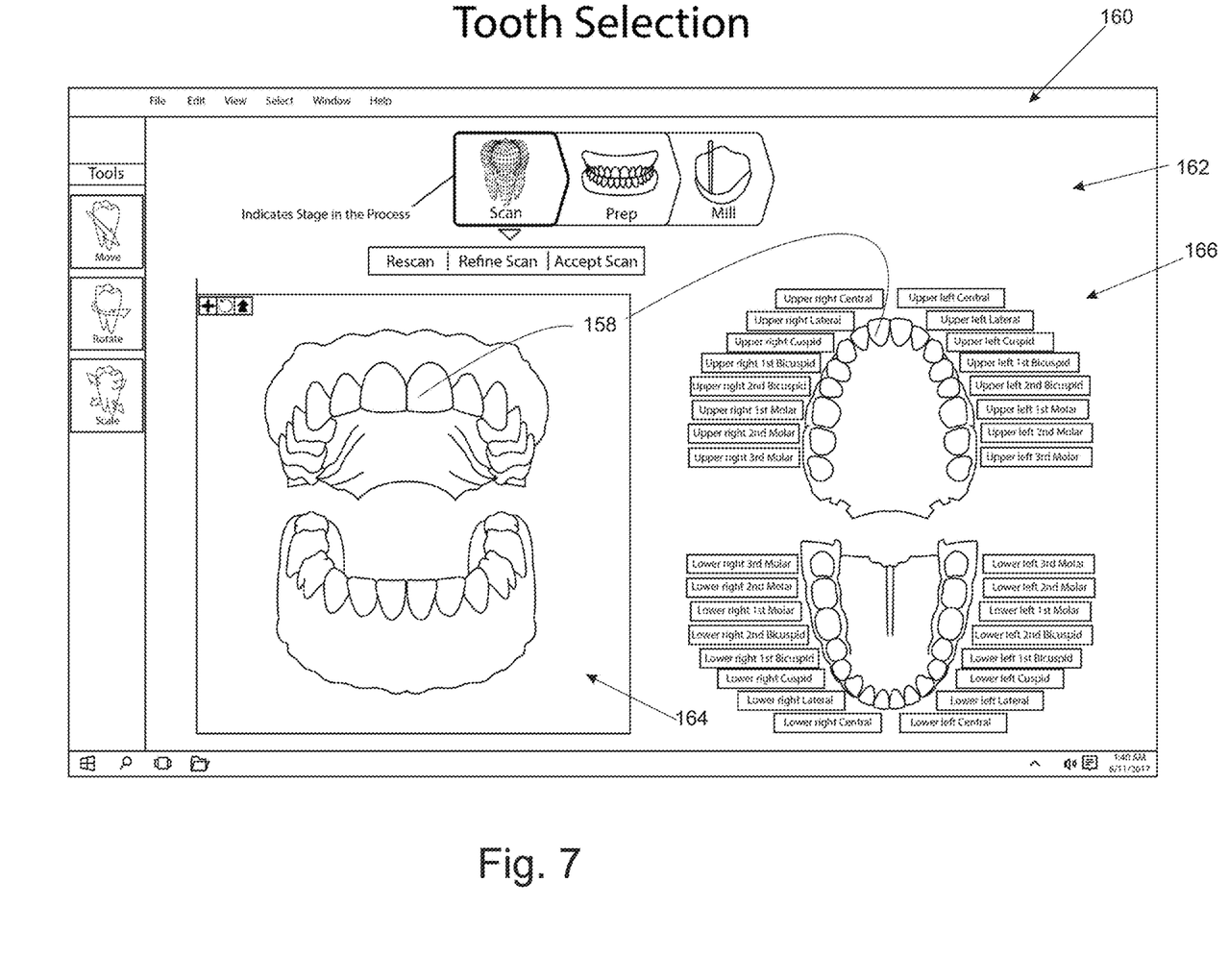
FIG. 7 provides a pictogram of all teeth in the upper and lower arch of a subject.

During operation of the dental treatment system, the user creates a patient profile entry. Such a profile includes the patient name, date of birth, patient number, and the like. The user is given the option of entering a treatment plan. In a refinement, the central processing unit renders a pictogram of all teeth in an upper and lower arch of the subject on the display as depicted in FIG. 7. Control program 20 also provides an onscreen prompt that allows the user to enter specific information above the teeth. Typically, this information is entered by clicking on specific teeth on the user interface. For example, missing teeth or the tooth on which surgery is to be performed are identified in this manner with descriptive notes being enterable. Moreover, the user can identify the type of restoration associated with the selected tooth such as crown, bridge, onlay/inlay, and filling (e.g., class 1 to 5). Control program 20 has the capability to make various suggestions to the user. For example, the central processing unit 12 presents to the user on display 24 (through execution of control program 20) a selection for teeth to place a modified rubber dam clamp on for a dental procedure and/or candidate teeth to scan.

Figure 8:
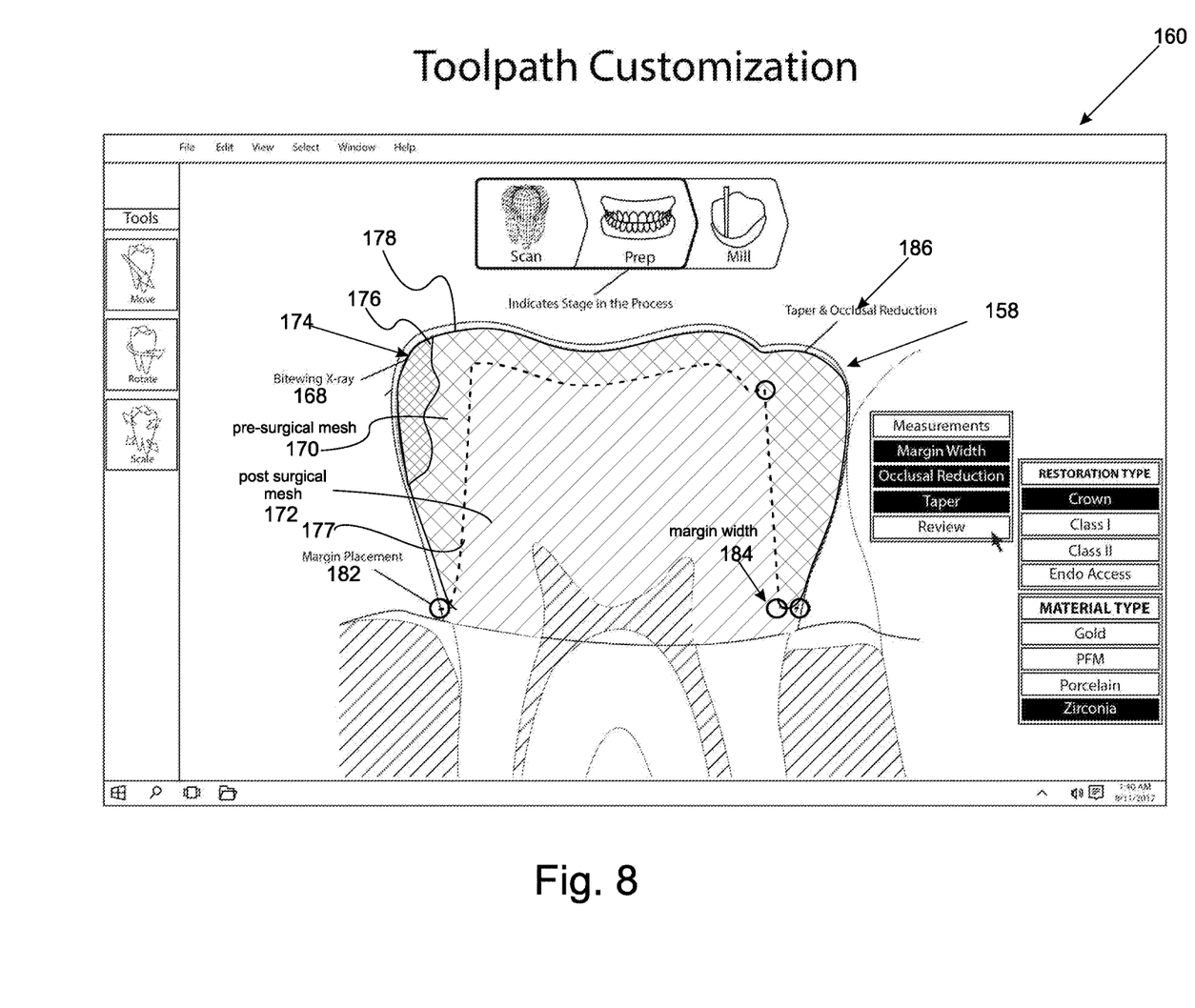
FIG. 8 illustrates a user interface displaying a radiograph registered to a 3D mesh representation of the tooth acquired from a 3d scanning system.
Figure 9:
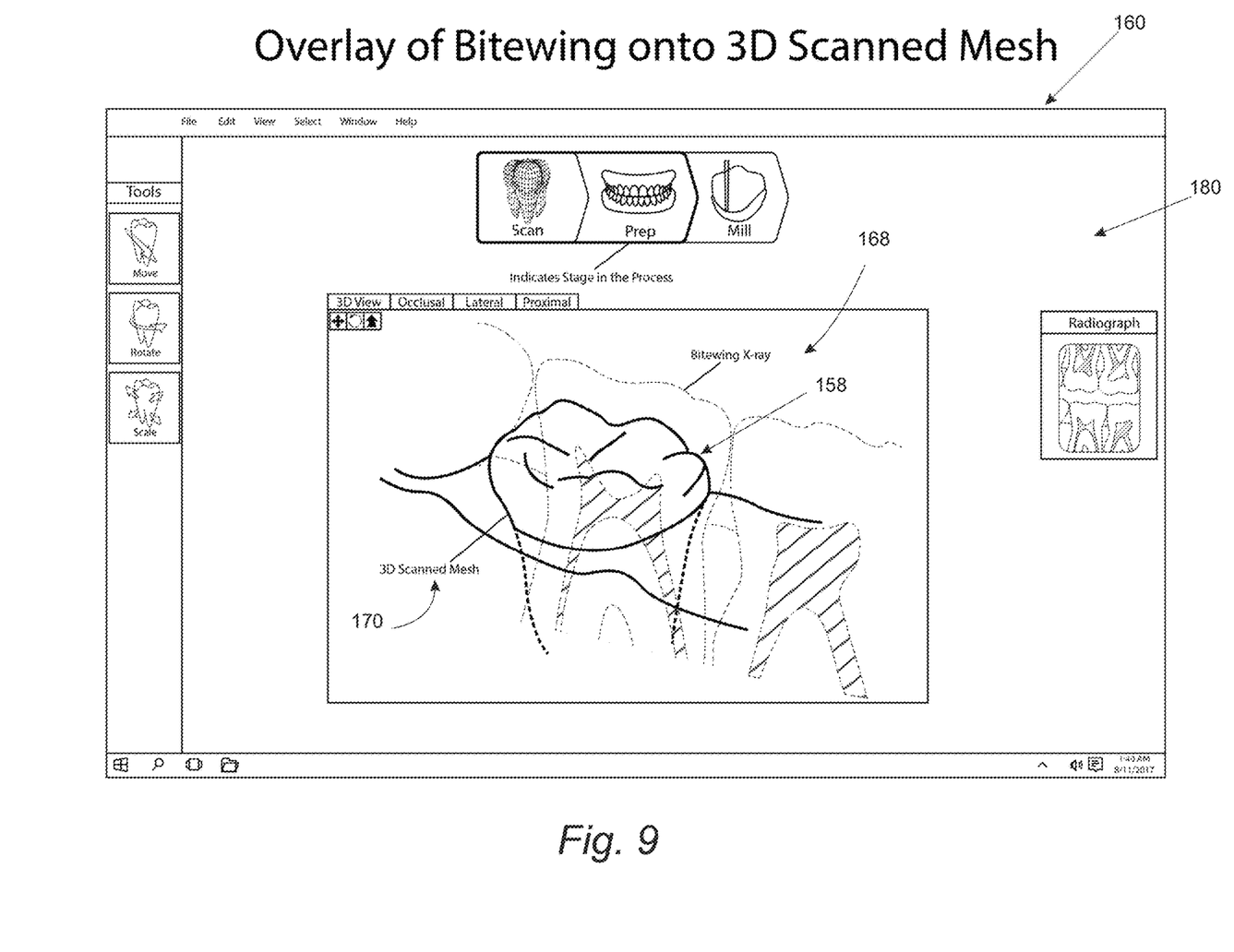
FIG. 9 displays a user interface for parametrically generating a tool path from 3 user clicks—click 1—the location of the external surface of the tooth to be prepared, click 2—the preparation margin width, click 3 captures both the taper and the occlusal reduction. The other parameters are determined when the user selects the tooth to be prepared and the restoration material.

Referring to FIG. 1, automated drill system 10 includes a dental tooth scanner 14 to create an image of the subject's tooth. An example of a dental tooth scanner is the iTero® Element which is an intraoral scanner commercially available from Align Technology, Inc. Such dental tooth scanners create an STL image file of the region of the patient's dental arches that are to be worked on. In particular, control program 20 creates a 3D image from the data received from dental tooth scanner 14. In a variation, central processing unit 12 renders a three dimensional model of the target tooth using a deformable pre-surgical mesh with a bitewing X-ray overlaid. The three dimensional model is typically presented on display 24. Advantageously, the deformable pre-surgical mesh is editable by the user to produce a postsurgical mesh and a representation of the target restoration (restoration mesh). The restoration mesh is generated with an inner surface that aligns the surface of the post-surgical mesh and an outer surface that represents the outer surface of the desired tooth restoration. Typically, during this editing, the tooth is not shaped as it is in a broken state, but as it should be in a pristine state which is designated as the completed restoration. The three dimensional model presents a rendering of surgical criteria to the user regarding treatment. Such surgical criteria include occlusal contacts, proximal contacts, anatomical morphology of the target tooth, occlusal reduction, margin placement relative to biological width and proximal contacts, and an image of a bite-wing superimposed onto the pre-surgical mesh. Occlusal contacts are the precise contact points on the completed restoration tooth anatomy where the upper and lower teeth contact one another. Therefore, the three dimensional model ensures that the restored teeth are positioned against the opposite teeth correctly. Proximal contacts relate to how the completed restoration touches the teeth on each side of it. Therefore, the three dimensional model ensures that the restored teeth fit correctly between the adjacent teeth. Finally, with respect to anatomical morphology, the three dimensional model ensures that the restored teeth look anatomically correct (e.g. cervical and buccal heights of contour). In addition, central processing unit 12 can display clinical information relevant to the surgical criteria. For example, as depicted in FIG. 8, the user interface displays tooth intersection points (labeled with item number 140) on the mesh. This allows the user to reduce or re-contour this area of the mesh to the give the correct contacts with opposing and adjacent teeth or anatomical shape (see, FIG. 8). The tool path is parametrically generated from a view port with a bitewing or periapical radiograph registered to the 3d mesh (see. FIG. 9). This allows the clinical to avoid anatomical landmarks such as the pulp, adjacent teeth, or remove caries. The tool path is then parametrically generated with 6 user inputs: tooth number being operated on, the restoration material which determines the material thickness required, the opposing dental arch mesh, and 3 clicks. The three clicks are (1—margin placement), 2 margin width, and 3 preparation wall taper and occlusal reduction.

Once parametrically generated tool path is approved by the dentist, it is used for the simultaneous milling of the restoration in the milling chamber concurrently while the robotic arm and end effector is cutting the tooth. It should be noted that the internal surface and margins of the filling are not milled until the tooth preparation shape is completed to ensure that the filling is made once the final internal structure is known. At this point, the only surface in question would be the mating/internal surface of the tooth being surgically cut and restoration being milled since the external surface of the restoration being milled is already known. The dentist or assistant than selects the material for the restoration to be milled based on their clinical assessment which may be present in the user interface. Various options include but are not limited to, composite blocks (inexpensive and fast to mill), lithium disilicate (slow to mill, very strong restoration), porcelain, and the like.

As set forth above, dental treatment system 10 includes at least one tooth scanner 14. In a variation, tooth scanner 14 can operate in several modes. Examples of such modes include, but are not limited to, surgical scan mode where a tooth requiring surgery and two adjacent teeth are imaged, occlusion scan mode in which teeth in an opposing arch of teeth that occlude with the teeth undergoing surgery, interdigitating scan in which a buccal/side scan mode with upper and lower teeth biting together are imaged to register how they fit together.

In certain variations, at least two scans of the subject's teeth will be performed. A first scan is performed before placement of the modified rubber dam and a second scan after placement of the modified rubber dam. With respect to the first scan, the user (e.g., a dental assistant) takes a 3D scan which acts a location map for our software. In a refinement, the user takes a scan of an area recommended by the control program 20. Regions recommended to scan depend on which teeth are being surgically treated. Typically, the scan can be a combination of a surgical scan, an occlusion scan, and/or an interdigitating scan. In a surgical scan, the tooth in question and the two teeth adjacent to it are scanned. In an occlusion scan, the teeth in the opposing arch of teeth that occlude (fit together with) with the teeth undergoing surgery are scanned. In an interdigitating scan, a buccal/side scan with the upper and lower teeth above biting together to register how they fit together is performed. The interdigitating scan image is used to register the position of how the upper and lower teeth scans fit together. With respect to the second scan, the user performs a second 3D scan with the rubber dam, rubber dam frame, modified rubber dam clamp, and passive positioning arm in place. Control program 20 registers or aligns the position of the two scans to create a combined 3D mesh. The combined 3D mesh images a tooth above the rubber dam, the tooth and gum tissue below the rubber dam, and the position of the modified rubber dam clamp positioning reference point.

Control program 20 is advantageously able to direct robotic arm 14 to perform surgery on multiple teeth. In particular, dental treatment system 10 is able to perform quadrant surgery. If the teeth are posterior teeth (from back molar to middle central incisor—International tooth number 1 to 8), scans are completed from posterior molars to the midline. This is called a quadrant in dentistry. Dental treatment system 10 is also able to perform anterior surgery. In particular, if the teeth are anterior teeth (tooth numbers 3-3), quadrants are not used. Instead, a grouping of anterior teeth is used of both upper and lower arches. For example, surgery on a tooth 46 would require a scan of the tooth in question and the two adjacent teeth (47, 46, and 45) as the surgical area the opposing teeth (15, 16, and 17). This surgery would also require a scan with the patient biting their teeth together from the side of approximately 15+45, 16+46, 17+47 to register how the teeth fit together. The scan process consists of the user (e.g., assistant) taking multiple pictures which include Z-value depth information which are stitched together to create a 3D model.

These scans can then be used to create a rotatable composite three dimensional model which is presented to the user. In this model, the user is able to set a preparation zone depending on the preparations type (e.g., crowns/onlays/inlays). In a refinement, the user can digitally paint different areas of the teeth with different "brushes" that signify the depth of cuts under each paint color. In another refinement, the user interacts with the 3d mesh using a haptic stylus input such as: the Geomagic Sculpt (www.geomagic.com/en/products/sculpt/touch/). The orientation of the cuts is perpendicular to the surface of the mesh which is painted or perpendicular to the occlusal plane. In a refinement, a preferred default value for the depth of the cuts is set as the default. In another variation "no-go" zones are set by the dentist and/or the control program 20. For example, 2D planes are set which go between the teeth and act as interproximal barriers to identify where one tooth starts and the next ends. This prevents the control software from extending cuts out of one tooth into another creating the working envelope. In this regard, the dentist sets gingival/gum margins by painting margins with a brush. In a variation, control program 20 is operable to determine the approximate location of a tooth's pulp and/or nerves. In one refinement, the determination is a probabilistic location based on radial distance from outer surface of tooth and likely depth to encounter the nerve.

In some variation, control program 20 requires an indication from the dentist to enable auto-extension of a dental preparation if decay is found during the surgical procedure. When decay is found, the user is presented with several options. The decay can be removed based on criteria set by the dentist. The decay can be left allowing the dentist to program an additional cycle of tooth cutting at this point in the program. The starting point of this cutting step is after the most recent tooth cut. This essentially re-runs the dentist input step using 3D models updated with the tooth status after the first pass of cutting. Problematic decayed areas can be highlighted in a different color on the 3D mesh. Details of when to remove decay can be given to the software. For example including settings to extend the preparation if it is close to what the dentist or software define as the space likely to contain the nerve. The software could be instructed to chase the decay into that space, or not to at the dentist's discretion. When a treatment plan has been finalized, the user provides an indication in the user interface that the treatment plan is accepted (i.e., checking a box, clicking a button, etc.)

After the user has completed editing of the three dimensional tool path, the central processing unit is operable to control the robotic arm to mill internal surface and margins of a target tooth in accordance to region's identified by the user in the three dimensional model. For example, the robotic arm 16 is operable to cut out an entire outline form shape as depicted by the user using digital brushes in the input device prior to starting the surgery. In this regard, the central processing unit 12 is operable to delay milling until a tooth preparation shape is completed.

The capture software of the scanner into the system software to allow access to the STL file generated. In a refinement, a dental technician takes a 3D scan to provide a location map. In particular, the technician takes a scan of the area recommended by the software. FIG. 5 provides an example of a chart of international tooth numbers and their positions to one another that can be used by the dentist.

In a refinement, the central processing unit 12 is operable to create a three dimensional density matrix of a subject's tooth to be treated by combining data received from the tooth imaging scanner with data received from the dental drill and/or the tooth scanner Specifically, the load of the motor driving the spindle will increase while cutting higher dentistry materials such as enamel, and decrease while cutting lower density materials such as caries. By combining the motor load (and indirectly spindle speed) with the feed rate of the tool, the 3d surface mesh of the tooth and the 3d coordinates of the end effector, we are able to calculate a relative density for each area being cut. In particular, central processing unit 12 is operable to identify volume units in the three dimensional density matrix and associate each volume unit associated with an identifier that characterizes a state of the tooth. Examples of such identifiers indicate if a region in the tooth includes hard enamel, decayed enamel, hard dentin, decayed dentin, solid cementum, decayed cementum, and pulp/nerve or a restorative material such as amalgam, composite, gold, and the like. Moreover, identifier may also be used to indicate previous filling (e.g., amalgam, composite, etc.) and previous crowns. Central processing unit 12 performs a predetermined treatment protocol on the volume unit depending on the identifier. The predetermined treatment protocols calculate the relative density of the tooth being cut by taking the milling speed, spindle speed of a bur in the end effector (or increase in current flow to the motor driving the spindle), and rate for moving the robotic arm. In this regard, central processing unit 12 is operable to direct the end effector of the robotic arm to cut a subject's tooth in accordance to regions identified in the three dimensional density matrix.

In a variation, dental treatment system 10 can also include a density scanner. Referring to FIG. 1, dental treatment system 10 further includes a density scanner 150 that creates a voxel based image (like a CT reconstruction). In such voxel images, the density of teeth is represented by colors. Moreover, the voxel image can be superimposed on the mesh. This display process is similar to CT images which use voxels instead of mesh to display density (radiopacity). However, in this variation, instead of using radiation opacity like CT, the density is determined as resistance to the cutting tool spinning. By combining the spindle speed of the end effector/electrical load on the motor, the known contact surface area of the end effector in contact with the mesh, the movement speed of the mesh relative to the tooth (taking into consideration relativistic speeds of the tooth encoded by the encoder arm), a value is calculated that is a relative density value. This value is compared to laboratory data from known density of test materials.

As the robotic arm cuts a tooth, a 3D matrix of density values is created and indexed to the XYZ coordinate of the end effector on the robotic cutting arm. The density value for each XYZ coordinate is calculated by using feed rate of the end effector relative to the patient's tooth and the surface area of the end effector bur in contact with the tooth. Since the 3D mesh of the tooth, the localized position of the bur relative to the tooth mesh, the shape of the burr, the burr's wear rate, and the spindle speed are known, the density value can be determined by correlation to a motor load. A tooth state matrix is built at the same XYZ coordinates. These states are calculated via an algorithm that combines the density values with their radial distance from the external surface of the tooth. This calculation takes advantage of the fact that teeth are composed of various materials layered in somewhat predictable positions. The position of the density value means different things in different areas of the tooth. For example an area discovered to have a low density spot relative to the adjacent areas could be a soft enamel zone, or the transition from hard enamel to a hard dentin zone depending on the radial position from the surface of the tooth. This difference is the difference between extending the preparation and maintaining it.

The decision to extend the tool path cycles through each marginal point on the tooth-restoration interface is determined by the state of tooth decay and the location of the coordinate in question (e.g., with the tool through the pre-defined no-go zones defined above (adjacent tooth, gums, pulp)). This cycle repeats until no additional decayed areas are detected, a boundary has been reached, or a call dentist item has been triggered.

With reference to FIGS. 7, 8, and 9, schematics of a user interface 160 displayed on a computer screen for the system of FIG. 1 are provided. FIG. 7 provides a screen shot used for tooth selection 172. Two view are provided in tooth selection 172—a three dimensional view 174 and a topographical layout view 176. A tooth 158 may be selected from this view. FIG. 8 provides a screen shot for overlay of the bitewing x-ray 168 onto the 3D scanned pre-surgical mesh 170. Post-surgical mesh 172 and restoration mesh 174 are also depicted. The restoration mesh 174 will include the surface defined by pre-surgical mesh 170 and the restoration that is to replace the missing tooth section 176. Moreover, restoration mesh 174 has an inner surface 177 that aligns to the postsurgical mesh 172 and an outer surface 178 that represents the desired restoration. FIG. 9 illustrates generation of the post-surgical mesh pre-op 180. The post-surgical mesh is used to create the toolpath. The post-surgical mesh is generated parametrically. In particular, margin placement 182 is determined by 1 (symmetrical margin placement) or 2 (non-symmetrical margin placement) clicks. The user clicks the mouse first (first, click) to indicate the coronal-apical height position on the exterior surface of the tooth 188 to place a surgical margin on the mesial. The superimposition on the bitewing x-ray 168 allows the user to ensure the margin in below any existing decay or previously existing restorative materials. The second mouse click determines the same data as point B for the distal margin. (note: margin placement 182 may be determined via an alternative process 0 this is one embodiment). The user is presented with a snap showing a range of acceptable locations on the exterior surface of the tooth 158 in which to place the margin. The software alerts the user if they select a margin position that encroaches on the biological width, or alternatively is above the contact point. These two boundaries serve as the snap range for the margin placement 182. The user then inputs the margin width 184 with one click—moving the mouse towards the center of the tooth to be treated in from the external margin placement 182. The user is then presented with a snap that allows the user to accept the ideal axial material reduction thickness. Alternatively, the user may disregard the snap and place the margin deeper into tooth tissue to capture decay or existing restorative material. Next, the user selects the taper of the tooth and the minimum reduction thickness 186 with the final click. Each material has minimum thickness requirements (i.e., reduction thickness). This thickness is achieved by articulating the upper and lower teeth meshes and subtracting the minimum thickness requirements from the height of the opposing tooth into the tooth that will be cut. This is done instead of just removing the minimum thickness from the tooth to be cut because certain parts of the tooth to be cut may be not in contact with the opposing tooth, meaning the gap space can be filled with the restorative material. This results in less tooth structure being removed. In the case of a severely worn surgical tooth, the superimposition of the bitewing x-ray 168 may indicate the post-treatment mesh extending on top of the pulp as shown in the anatomical image (bitewing radiograph). In this case, the clinical and inform the patient of the potential need for a root canal or alternatively complete the root canal prophylactically. The user is presented with a snap that indicated the software calculated ideal taper and reduction thickness 186. The user may accept this snap or change it to her/his desired locations.

Figure 10:
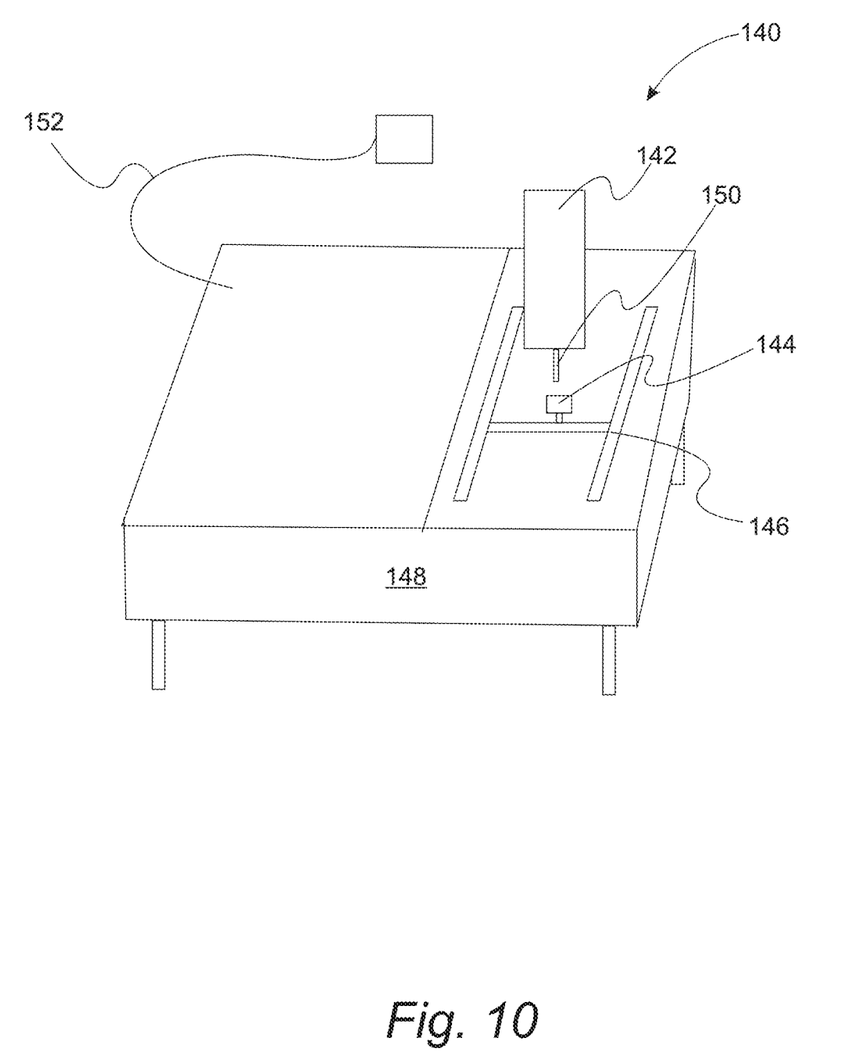
FIG. 10 provides a schematic of a milling station for creating dental restorations.

With reference to FIG. 10, a schematic illustration of milling station for preparing a dental restoration to be placed in the subject is provided. The system set forth above is described as performing dental surgery on a patient (i.e., drilling). The inclusion of a milling station in the system of FIG. 1 allows for these restorations to be manufactured. Dental system treatment 10 determines the parameters for performing dental surgery. Moreover, during the execution of this surgery, the tooth scanner is used to monitor the surgery and determine is additional tooth areas need to be included. Therefore, dental system treatment 10 is also able to calculate the desired shape of the dental component to be placed in a patient (e.g., filling, inlay, crown). Milling station 140 includes milling component 142 which operates on workpiece 144 to create the dental restoration. In variation, milling component 142 is a robotic arm similar robotic arm 16 of FIG. 1. In a refinement, milling component 142 is similar to a conventional mill which can be translated along the Z direction. In this latter variation, work piece 114 is attached to XY translational system 146. XY translational system 146 is mounted on table 148. The milling tool 150 of mill 142 is moveable in the Z direction. Cable 152 is used to connect milling station 140 to central processing unit of FIG. 1. In a refinement, the central processing unit 12 is operable to control the robotic arm to simultaneously mill a restoration with allowances for changes in the internal mating surface of the restoration and possible external shape changes as the size of the restoration increases to include portions of the external surface that were not to be replaced at the procedure's onset.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for performing dental surgery on a subject, the system comprising:
    a density scanner creating a voxel image of a target tooth representing a density value of a target tooth, the density value comprising a radial distance from the external surface of the target tooth;
    a central processing unit having a computer memory encoded with a control program to render a three dimensional model of a target tooth from the voxel image and create an application that controls automated operation of the system, the three dimensional model including a post-surgical tooth mesh and a restoration mesh, wherein generation of the post-surgical tooth mesh and the restoration mesh incorporates a minimum material thickness, and wherein the minimum material thickness is determined by articulating a target tooth mesh with an opposing tooth mesh and subtracting a minimum thickness requirement of the target tooth from a height of the opposing tooth mesh;
    an input device that receives surgical instructions from a user for providing the surgical intervention, the input device comprising a display for depicting the three dimensional model of the target tooth, the surgical instructions comprising selection of a positioning reference point corresponding to a position of a clamp, wherein the surgical instructions are received by the central processing unit; and
    a robot in communication with the central processing unit, the robot including an end effector for performing dental surgery, wherein the central processing unit controls the robot to remove a region of the target tooth based on the surgical instructions, the voxel image, a motor load of the end effector, coordinates of the end effector, and a feed rate of the end effector.

2. The system of claim 1, further comprising an encoder that tracks a motion of the subject's head and tooth, wherein the encoder is configured to trigger a shutdown procedure.

3. The system of claim 1, wherein the end effector is numerically controlled.

4. The system of claim 1, wherein the central processing unit renders a pictogram of all teeth in an upper and lower arch of the subject on the display.

5. The system of claim 1, further comprising a tooth scanner that transfers tooth image data to the central processing unit.

6. The system of claim 5, wherein the tooth scanner operates in a mode selected from the group consisting of a surgical scan mode where a tooth requiring surgery and two adjacent teeth are imaged, an occlusion scan mode in which teeth in an opposing arch of teeth that occlude with the teeth undergoing surgery are imaged, and an interdigitating scan in which a buccal/side scan mode with upper and lower teeth biting together are imaged.

7. The system of claim 1, wherein the central processing unit renders the three dimensional model of the target tooth using a deformable pre-surgical mesh, the deformable pre-surgical mesh being editable by the user to produce the post-surgical tooth mesh and the restoration mesh.

8. The system of claim 7, wherein the three dimensional model includes a rendering of a surgical criteria.

9. The system of claim 7, wherein a bitewing X-ray overlays the pre-surgical mesh.

10. The system of claim 1, wherein the restoration mesh comprises an inner surface aligning to the post-surgical tooth mesh and an outer surface representing a desired restoration.

11. The system of claim 1, wherein the robot is operable to cut out an outline form shape as depicted by the user using the input device.

12. The system of claim 1, wherein the central processing unit is operable to create a three dimensional density matrix of the target tooth.

13. The system of claim 12, wherein the central processing unit is operable to identify volume units in the three dimensional density matrix, each volume unit associated with an identifier that characterizes a state of the tooth, the central process unit being operable to direct the end effector of the robot to cut a subject's the tooth in accordance to regions identified in the three dimensional density matrix.

14. The system of claim 13, wherein the identifier indicates if a region in the tooth includes hard enamel, decayed enamel, hard dentin, decayed dentin, or a restorative material, the central processing unit being operable to perform a predetermined treatment protocol on the volume unit depending on the identifier.

15. The system of claim 8, wherein the surgical criteria comprise one or more of: occlusal contacts, proximal contacts, anatomical morphology of the target tooth, occlusal reduction, margin placement relative to biological width and proximal contacts, and an image of a bite-wing superimposed onto the pre-surgical mesh.

16. The system of claim 1, wherein surgical instructions further comprise selection of a restoration material.

17. The system of claim 1, wherein a minimum thickness requirement is determined by a restoration material.

18. The system of claim 2, wherein the encoder comprises an encoder arm to attach to the clamp.

19. The system of claim 1, wherein the robot further comprises a tool changer for the automatic changing of end effectors to match an appropriate end effector with allowances for changes in the dental surgery that were not to be performed at an onset of the dental surgery.

* * * * *